US005589396A

United States Patent [19]
Frye et al.

[11] Patent Number: 5,589,396
[45] Date of Patent: * Dec. 31, 1996

[54] COATINGS WITH CONTROLLED POROSITY AND CHEMICAL PROPERTIES

[75] Inventors: Gregory C. Frye, Bernalillo County; C. Jeffrey Brinker, Albuquerque; Daniel H. Doughty, Albuquerque; Thomas Bein, Albuquerque; Karin Moller, Albuquerque, all of N.M.

[73] Assignee: Sandia Corporation, Albuquerque, N.M.

[*] Notice: The term of this patent shall not extend beyond the expiration date of Pat. No. 5,224,972.

[21] Appl. No.: 11,518

[22] Filed: Feb. 1, 1993

Related U.S. Application Data

[63] Continuation of Ser. No. 686,548, Apr. 18, 1991, Pat. No. 5,224,972, which is a continuation-in-part of Ser. No. 580,373, Sep. 11, 1990, Pat. No. 5,151,110.

[51] Int. Cl.⁶ .................................................. B01D 53/04
[52] U.S. Cl. ........................ 436/73; 436/72; 422/69; 422/82.01; 422/82.02; 422/82.04; 422/83; 96/154; 95/902
[58] Field of Search ................................... 55/18–21, 67, 55/74, 197, 208, 270, 274, 386, 389, 524, 387; 422/82.1–82.04, 83, 69, 56, 57; 436/72, 73

[56] References Cited

U.S. PATENT DOCUMENTS

| | | | |
|---|---|---|---|
| 3,164,004 | 1/1965 | King | 73/23 |
| 3,891,413 | 6/1975 | Stevens et al. | 55/67 |
| 4,029,583 | 6/1977 | Chang et al. | 55/386 X |
| 4,140,653 | 2/1979 | Imura et al. | 55/386 X |
| 4,277,322 | 7/1981 | Kane | 204/195 S |
| 4,335,017 | 6/1982 | Miles et al. | 55/386 X |
| 4,348,296 | 9/1982 | Bauman et al. | 55/386 X |
| 4,348,297 | 9/1982 | Bauman et al. | 55/386 X |
| 4,504,522 | 3/1985 | Kaiser et al. | 427/103 |
| 4,520,122 | 5/1985 | Arena | 55/386 X |
| 4,652,280 | 3/1987 | Boeren et al. | 55/386 X |
| 4,782,040 | 11/1988 | Revis et al. | 55/386 X |
| 4,782,042 | 11/1988 | Revis et al. | 502/401 |
| 4,834,496 | 5/1989 | Blyler, Jr. et al. | 350/96.29 |
| 4,847,594 | 7/1989 | Stetter | 350/540 |
| 4,886,740 | 12/1989 | Vadgama | 435/4 |
| 4,950,634 | 8/1990 | Williams et al. | 55/386 X |
| 4,950,635 | 8/1990 | Williams et al. | 55/386 X |
| 5,151,110 | 9/1992 | Bein et al. | 55/75 |

OTHER PUBLICATIONS

Ricco, et al., "Determination of BET Surface Areas of Porous Thin Films Using Surface Acoustic Wave Devices," *Langmuir*, vol. 5, p. 273 (1989).

Brinker, et al., "Better Ceramics Through Chemistry III," *Materials Research Society Symposium Proceedings*, vol. 121 (1988) Textbook.

Frye, et al., "Characterization of the Surface Area and Porosity of Sol–Gel Films Using SAW Devices," *Materials Research Society Symposium Proceedings*, vol. 121, pp. 349–354 (1988).

Martin, et al.; "Characterization of SH Acoustic Plate Mode Liquid Sensors," *Sensors and Actuators*, vol. 20, pp. 253–268) (1989).

Frye, et al., "Controlled Microstructure Oxide Coatings for Chemical Sensors," *Proc. 1990 Solid–State Sensor and Actuator Workshop*, p. 61, IEEE, New York 1990.

(List continued on next page.)

*Primary Examiner*—Jill Warden
*Assistant Examiner*—Harold Y. Pyon
*Attorney, Agent, or Firm*—Peacock & Meyers; George H. Libman

[57] ABSTRACT

Coatings and sensors having both steric and chemical selectivity. Controlled porosity provides the steric selectivity, whereas chemically tailored film properties, using controlled composition or modification by coupling agents, chemical species replacement, or chemical species within pores, provide the chemical selectivity. Single or multiple layers may be provided.

23 Claims, 5 Drawing Sheets

OTHER PUBLICATIONS

Lynch, *CRC Handbook of Materials Science*, p. 198, CBC Press, Boca Raton, FL (1975).

Frye, et al., "Dual Output Surface Acoustic Wave Sensors for Molecular Identification", *Sensors and Materials*, vol. 2, pp. 187–195 (1991).

Ku, et al., "Electrical Properties of Polymers—Chemical Principles," pp. 7–10 (1987).

Frye, et al., "Materials Characterization Using Surface Acoustic Wave Devices," *Applied Spectroscopy Reviews*, vol. 26 (1&2), pp. 73–149 (1991).

Moller, et al., "Oxometalate–Glass Composition and Thin Films", *Materials Research Society Symposium Proceedings*, vol. 180 (1990).

Bein, et al., "Molecular Sieve Sensors for Selective Detection at the Nanogram Level," *Journal of the American Chemical Society*, vol. III, pp. 7640–7641 (1989).

Carey, et al., "Multicomponent Analysis Using an Array of Piezoelectric Crystal Sensors," *Anal. Chem.*, vol. 59, pp. 1529–1534 (1987).

Carey, et al., "Monitoring a Dryer Operation Using an Array of Piezoelectric Crystals," *Anal. Chem.*, vol. 60, pp. 541–544 (1988).

Jaffe, et al., *Piezoelectric Ceramics*, Academic Press, London and New York (1971).

Janata, Principles of Chemical Sensors, Plenum Press, New York and London, pp. 56–69 (1989).

Frye, et al., "Sol–Gel Coatings on Acoustic Wave Devices; Thin Film Characterization and Chemical Sensor Development," *Material Research Society Symposium Proceedings*, vol. 180, pp. 583–593 (1990).

Brinker, et al., *Sol–Gel Science; The Physics and Chemistry of Sol–Gel Processing*, Academic Press, Inc., pp. 787–835 (1990).

Nieuwenhuizen, et al., "Surface Acoustic Wave Chemical Sensors," *Sensors and Materials*, vol. 1, No. 5, pp. 261–300 (1989).

Cotton, et al.; "Advanced Inorganic Chemistry, Fifth Edition"; Wiley, New York (1988).

"Advances in Sensor Technology Promise Reduced Risk From Toxic Substrates"; News Release; *Materials Research Society*; pp. 105; (Apr. 1990).

Olson; "Atlas of Zeolite Structure Types"; 2nd Edition; Butterworths: London (1987).

"Science/Technology Concentrates"; C&EN; p. 32; Sep. 25, 1989.

"Chemical Sensors Play Growing Role in Analytical Sciences"; C&EN; pp. 24–26; Jan. 29, 1990.

Chemecology; vol. 19, No. 2, p. 5, Mar. 1990.

"Zeolite Sensors Cut Monitoring Costs"; *MRS Bulletin* May 1990; vol. 15, No. 5.

Brinker, et al.; "Sol–Gel Thin Film Formation"; *Proc. IVth Workshop on Gels*.

Inside R&D, vol. 19, No. 16, Apr. 18, 1990.

Avnir, et al.; "The Nature of the Silica Cage As Reflected by Spectral Changes and Enhanced Photostability of Trapped Rhodamine 6G" *J. Phys. Chem.*, vol. 88, (1984) pp. 5956–5959.

Avnir, et al.; "Organic Fluorescent Dyes Trapped in Silica Structural and Silica–Titania Thin Films by the Sol–Gel Method. Photophysical, Film and Cage Properties"; *Journal of Non–Crystalline Solids*, vol. 74 (1985) pp. 395–406.

Kaufman, et al.; "A Photophysical Study of the Sol/Gel Transition in Silica: Structural Dynamics and Oscillations, Room–Temperature Phosphorescence and Photochromic Gel Glasses"; *Journal of Non–Crystalline Solids*, vol. 82 (1986) pp. 103–109.

Kaufman, et al.; "Prolonged Chaotic Oscillations During the Gel/Xerogel Transition in Silicon Tetramethoxide Polymerization as Detected by Pyrene Excimerization"; *Mat. Res. Soc. Symp. Proc.*, vol. 73 (1986) pp. 145–156.

Kaufman, et al.; "Structural Changes Along the Sol Gel–Xerogel Transition in Silica As Probed by Pyrene Excited–State Emission"; *Langmuir*, vol. 2 (1986) pp. 717–722.

Pouxviel, et al.; "Fluorescence Study of Aluminosilicate Sols and Gels Doped with Hydroxy Trisulfonated Pyrene"; *J. Phys. Chem.*, vol. 93 (1989) pp. 2134–2139.

Pope, et al; "Incorporation of Organic Dyes In Polymer/Oxide Composites"; *MRS Bulletin*, Mar. 17/May 15, 1987, pp. 29–31.

Tani, et al.; "Photochemical Hole–Burning Study of 1,4–dihydroxyanthraquinone Doped in Amorphous Silica Prepared by Alcoholate Method"; *J. Appl. Phys.*, vol. 58, No. 9 (Nov. 1, 1985) pp. 3559–3565.

Makishima, et al.; "Preparation of Amorphous Silicas Doped with Organic Molecules by the Sol–Gel Process"; *J. Am. Cerem. Soc.*, vol. 69, [4] C–72–C–74 (1986).

Nogues, et al.; "Porous Gel–Silica, A Matrix For Optically Active Components"; *Journal of Non–Crystalline Solids*, vol. 121 (1990) pp. 136–142.

Reisfeld, et al.; "Transparent High Surface Area Porous Supports As New Materials For Laminescent Solar Concentrators"; *Solar Energy Materials*, vol. 8, (1983) pp. 399–409.

Bagnall, et al; "The Use of Solution Impregnation to Dope Silica Gels with Cd, Se and S"; *Journal of Non–Crystalline Solids*, vol. 121 (1990) pp. 221–226.

Ikoma, et al.; "Compartive Studies on the Silica Gels Doped with Polyamine Copper(ii) Complexes by Ion–Exchange and Sol–Gel Techniques"; *Journal of Non–Crystalline Solids*, vol. 113 (1989) pp. 130–136.

Ikoma, et al.; "Characterization of Polyamine Copper (II) Complex–Doped Alumina Gels Prepared by the Sol–Gel Technique"; *Journal of Non–Crystalline Solids*, vol. 122 (1990) pp. 183–192.

Slama–Schwok, et al.; "Photoinduced Charge Separation Across the Solid–Liquid Interface of Porous Sol–Gel Glasses: Catalyzed Hydrogen Generation from Water"; *J. Phys. Chem.*, vol. 93 (1989) pp. 7544–7547.

Chernyak, et al.; "Oxazine–170 in Sol–Gel and PMMA Films as a Reversible Optical Waveguide Sensor for Ammonia and Acids"; *Sensors and Materials*, vol. 2, No. 1 (1990) pp. 117–126.

Zusman, et al.; "Doped Sol–Gel Glasses as Chemical Sensors"; *Journal of Non–Crystalline Solids*, vol. 122 (1990) pp. 107–109.

Novak, et al.; "Vycor Porous Glass (Thirsty Glass) as a Reaction Medium For Optical Waveguide Based Chemical Vapor Detectors"; *Spectroscopy Letters*, vol. 21(2) (1988), pp. 127–145.

Knobbe, et al.; "Organic Molecules Entrapped in a Silica Host for use as Biosensor Probe Materials"; *SPIE Optical Fibers in Medicine III*, vol. 906 (1988) pp. 39–41.

Labuda; "Chemically Modified Electrodes as Sensors in Chemical Analysis"; *Journal of Analytical Chem. of USSR*, vol. 45, No. 4 (1990) pp. 445–455.

COATINGS WITH CONTROLLED POROSITY AND CHEMICAL PROPERTIES

GOVERNMENT RIGHTS

The U.S. Government has rights to this invention pursuant to contract No. DE-AC04-76DP00789, between the Department of Energy and the American Telephone and Telegraph Company.

This is a continuation of application Ser. No. 07/686,548 filed Apr. 18, 1991, now U.S. Pat. No. 5,224,972, which is a continuation in part of Ser. No. 07/580,373 filed Sep. 11, 1990, now U.S. Pat. No. 5,151,110.

BACKGROUND OF THE INVENTION

1. Field of the Invention (Technical Field)

The present invention relates to modified inorganic coatings and methods for producing and using such coatings, particularly useful as chemical sensors. These coatings provide a combination of both chemical and steric selectivity to select among various chemical species.

2. Background Art

Determining and/or monitoring the presence of certain chemical species within an environment, e.g., pollutants, toxic substances, and other predetermined compounds, is becoming of increasing importance with respect to such fields as health, environmental protection, resource conservation, and chemical processes.

There exist very sophisticated and complicated systems which are capable of detecting the presence of, for example, a substance in the atmosphere, even down to as low a level as a trillionth of a gram. However, many devices are impractical for field applications. For example, in analyzing water or soil samples for the presence of harmful substances, the samples are generally collected from the field and then taken to the lab and subjected to analysis using, for example, a gas or liquid chromatograph and/or a mass spectrometer. These types of analysis equipment, while very sophisticated and precise, are not practical for use in the field, require a substantial capital investment, and often take a long period of time for completion of the analysis, i.e., often up to several days.

Chemical and biochemical sensors, which are less expensive and smaller in size than those discussed above, also can provide for determining and/or monitoring the presence of certain chemical species in an environment. Many chemical sensors consist of a thin coating (e.g., a polymer film) which selectively sorbs the chemical species of interest and a sensing device to detect this sorption and convert it into a monitorable signal. A review of coating materials used in this way with surface acoustic wave sensors is given in M. S. Nieuwenhuizen, et al., "Surface Acoustic Wave Chemical Sensors," *Sensors and Materials*, Vol. 1, pp. 261–300 (1989). The sensitivity of the sensor is determined by the sensitivity of the detecting device to the perturbation in film properties and by the total sorption capacity of the coating.

One class of chemical sensor is generally known as a piezoelectric sensor, such as surface acoustic wave (SAW), acoustic plate mode (APM), or quartz crystal microbalance (QCM) devices. These sensors are based on a piezoelectric substrate and are also called gravimetric sensors, due to their ability to detect a change in mass in a coating formed on the device surface. SAW sensors are discussed in detail in M. S. Nieuwenhuizen, et al., Ibid. By employing an alternating voltage to an interdigital transducer formed on the piezoelectric crystal, there results a surface acoustic wave. The propagation velocity of this surface acoustic wave is a sensitive probe of changes in the properties of the coating material. Coating properties which are known to elicit a detectable SAW sensor response are mass (i.e., as determined by the thickness and density of the coating), elasticity, viscoelasticity, conductivity, and dielectric constant (G. C. Frye and S. J. Martin, "Materials Characterization Using Surface Acoustic Wave Devices," E. G. Brame, Jr., Editor, *Applied Spectroscopy Reviews* (1991)). Changes in these properties can also result in changes in the attenuation (i.e., loss of acoustic power) of the wave. In some situations, monitoring attenuation may be preferable to monitoring velocity or, alternatively, it has been found that there are some situations where simultaneously monitoring both velocity and attenuation can be useful (G. C. Frye and S. J. Martin, "Dual Output Surface Acoustic Wave Sensors for Molecular Identification," *Sensors and Materials*, Vol. 2, pp. 187–195 (1991)). Thus, when a substance sorbs into a coating formed on the surface of a SAW device, there is produced a response. To indicate their sensitivity, SAW devices are capable of detecting mass changes as low as about 100 pg/cm$^2$. APM devices, discussed in detail in S. J. Martin, et al., *Sensors and Actuators*, "Characterization of SH Acoustic Plate Mode Liquid Sensors," Vol. 20, pp. 253–268 (1989), are similar to SAW devices except the acoustic wave used can be operated with the device in contact with a liquid. Similarly, an alternating voltage applied to the two opposite electrodes on a QCM (typically AT-cut quartz) device induces a thickness shear mode whose resonance frequency changes in proportion to mass changes in a coating material. However, while these piezoelectric devices are very sensitive detectors, especially for mass, they are not inherently selective with respect to different substances.

There are a variety of other chemical sensors, such as optical sensors, where a sensor response is produced when there is a change in the properties of the sensor coating.

Sensor selectivity, the ability to detect a chemical species in an environment containing other chemical species, is generally determined solely by the ability of the coating to specifically sorb the species to be detected to the exclusion of all others. For most coatings, some selectivity is obtained based solely on providing stronger chemical interactions between the coating and the target species than occur between the coating and the species which are not to be detected. (M. S. Nieuwenhuizen, et al., Ibid.)

Several references, discussed below, disclose porosity and/or chemical sorption; however, none of these references relate to the combination of controlled porosity and chemical selectivity.

U.S. Pat. No. 3,164,004, to King, Jr, entitled *Coated Piezoelectric Analyzers*, discloses a variety of coating materials for use with the piezoelectric sensors typically called quartz crystal microbalances. Included in these coating materials are a few porous materials: silica gel, alumina, and molecular sieves. These materials are listed simply as sorbents for water, and the use of controlled pore size for discrimination is not mentioned. In addition, as described, these materials do not have tailored surface chemistry for providing chemical selectivity.

U.S. Pat. No. 4,847,594, to Stetter, entitled *Sensor for Detecting the Exhaustion of an Adsorbent Bed*, relates to a chemiresistor for use in monitoring breakthrough of a gas mask adsorbent bed. The sensor uses a vapor adsorbing coating which consists of carbon embedded in a silicone film. Although porous, this carbon does not have a tailored surface chemistry, nor is the porosity used as a method for obtaining selectivity.

U.S. Pat. No. 4,834,496, to Blyler, Jr., et al., entitled *Optical Fiber Sensors for Chemical Detection*, discloses an optical fiber sensor which uses coatings consisting of optically active species (e.g., fluorescent dyes) contained in a permeable polymer coating around the fiber.

U.S. Pat. No. 4,504,522, to Kaiser, et al., entitled *Method of Making a Titanium Dioxide Oxygen Sensor Element by Chemical Vapor Deposition*, describes a chemical vapor deposition technique for titanium dioxide films to be used as automotive oxygen sensors. These films have porosity; however, the scale of this porosity is much too large to provide size exclusion. Oxygen is sensed due to its reaction with the film material rather than any selective adsorption by the material surfaces.

U.S. Pat. No. 4,277,322, to Kane, entitled *Oxygen Sensor*, discloses the use of a porous ceramic filler to protect a platinum sensor element. The porosity is not used for selectivity.

Parent application Ser. No. 07/580,373 now U.S. Pat. No. 5,151,110 relates to steric based selectivity using a different type of coating containing small crystals of zeolites embedded in a dense silicate matrix. These zeolites have a crystalline pore structure with uniform sized openings. Molecules smaller than the openings showed large sensor responses due to sorption on the surfaces of the zeolite pores while species too large to have access to the pores due to their larger size showed a much smaller sensor response (also see T. Bein, et al., "Molecular Sieve Sensors for Selective Detection at the Nanogram Level," *Journal of the American Chemical Society*, Vol. 111, pp. 7640–41 (1989)).

SUMMARY OF THE INVENTION
(DISCLOSURE OF THE INVENTION)

The present invention relates to coatings and methods for making and using coatings. The coatings provide selectivity among different chemical species.

The preferred coating of the invention comprises pores having a predetermined uniform pore size, the predetermined uniform pore size sufficient to prevent analyte species of larger size than the pores from entering the pores and the predetermined uniform pore size sufficient to allow analyte species of smaller size than the pores to enter the pores; and chemically sorbing (preferably within the pores) at least a portion of the analyte species having a smaller size than the pores. The coating is preferably made by sol-gel techniques to form the predetermined uniform pore size. The coating is preferably made of various materials, such as silica, titania, zirconia, or alumina.

In the preferred embodiment, a chemically reactive species is attached to the coating, such as by a coupling agent. This chemically reactive species is reactive to the analyte species to be sorbed within the pores. The chemically reactive species may comprise a chelating agent. If the coating is a silicate film, a silane coupling agent may be utilized to attach the chemically reactive species to the silicate film. Useful silane coupling agents include $LSiX_3$ and $LSi(OR)_3$ wherein X is a halide, OR is an alkoxide group, and L is an attached group.

In an alternative embodiment, a portion of surface molecules in the film are replaced with chemically reactive species, the chemically reactive species reactive to the analyte to be sorbed within the pores. The chemically reactive species may comprise a metal, such as aluminum, using a metal alkyl, such as trimethylaluminum, to replace surface molecules with the metal.

In yet another alternative embodiment, chemical sorption is provided by using a chemically reactive species adjacent the coating and seated within the pores. The chemically reactive species may be trapped within the pores due to their size being larger than the size of the entrance to the pores. The chemically reactive species seated within the pores may exhibit selective ion exchange properties. Polyoxometalate species are particularly useful in this embodiment.

In another embodiment, the coating comprises a hydrous oxide, such as sodium titanate and sodium niobate. These materials can be made porous as deposited and the cation used (e.g., titanium vs. niobium) determines the chemical interactions which will result in chemical selectivity in the ion exchange properties of the material.

The coating may comprise a single layer or multiple layers. With multiple layers, at least one layer may provide the pores and at least one other layer may provide the chemical sorption of the analyte species.

The preferred coating has a thickness of between approximately 0.1 µm and 10 µm, and most preferably a thickness of between approximately 0.1 µm and 2 µm. The preferred diameter of the pores is between approximately 0.1 nm and 10 nm, and most preferably between approximately 0.2 nm and 1 nm.

The invention further relates to a selective chemical sensor comprising the coating, discussed above, disposed on a sensor substrate. The substrate preferably comprises a piezoelectric substrate capable of detecting mass changes resulting from sorption of material thereon. An alternating voltage, which is applied to a transducer connected to the piezoelectric surface, may also be provided. The piezoelectric element preferably comprises a surface acoustic wave (SAW) device, an acoustic plate mode (APM) device, or a quartz crystal microbalance (QCM) device.

The invention further relates to a method of selectively detecting the presence of a chemical entity within an environment comprising placing a selective chemical sensor, such as described above, in the environment and detecting changes in the coating resulting from sorption of material thereon. The environment may be gaseous or liquid. More than one sensor may be provided.

The invention further relates to a method of making a selective chemical sensor. The method comprises the steps of:

a) providing a sensor substrate; and b) disposing the coating, discussed above, on the sensor substrate.

An object of the invention, therefore, is to provide sensitive and selective coatings and chemical sensors and methods of making and using the same, wherein the sensor is both inexpensive to produce and suitable for field applications.

Another object of the invention is to provide a sensor with a short time analysis and capable of selective detection of substances at a nanogram level.

Yet another object of the present invention is to provide coatings and sensors based on both steric and chemical selectivity.

An advantage of the present invention is that species having similar sizes or similar chemical reactivities can be discriminated from one another.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

Figure 1:
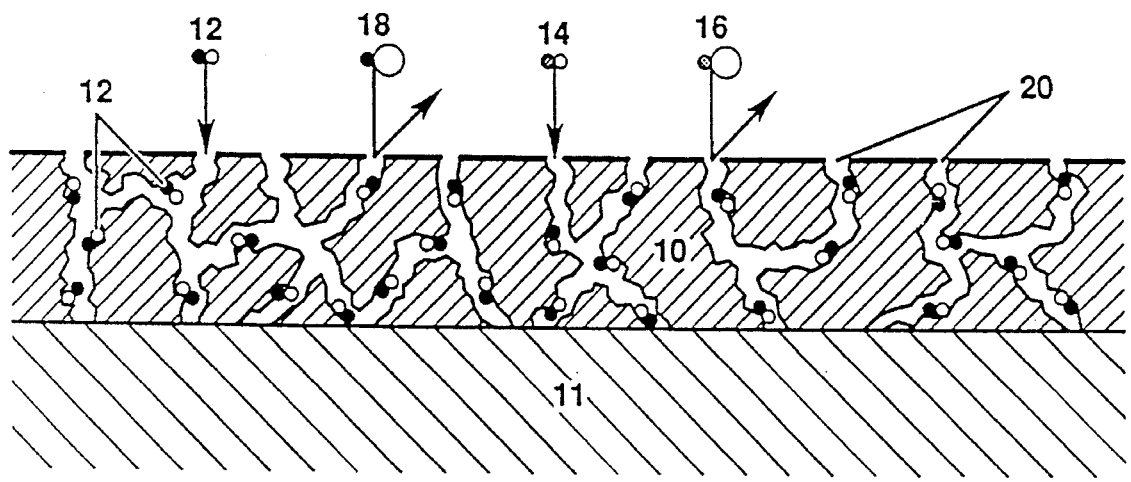
FIG. 1 is an illustration of a sensor having a coating of the present invention, allowing steric and chemical selectivity of chemical species B-C in the presence of species A-C, A-D, and B-D.

DESCRIPTION OF THE PREFERRED EMBODIMENTS (BEST MODES FOR CARRYING OUT THE INVENTION)

The present invention relates to modified inorganic coatings, particularly useful as a discriminating element in acoustic wave (AW) sensors. These coatings, preferably modified sol-gel coatings, are tailored to impart chemical and steric selectivity to AW sensors. Chemical selectivity is imparted by surface modification, novel composition coatings, or entrapped species, whereas steric selectivity is imparted by providing tailored porosity and pore size distribution. The combination of these two effects provides improved discrimination and, therefore, greater selectivity. In the present invention, the sorption is focused at the surfaces and, thus, the large surface areas attainable result in highly sensitive sensors.

The following terms have the following definitions throughout the specification and claims. "Species" or "entity" are intended to include chemical and ionic species, atoms, molecules, ions, compounds, and the like. "Chemical selectivity," "chemical selection," "chemical interaction," "binding," "absorption," "adsorption," and "sorption" and variations are interchangeable and are intended to include any type of interaction of a chemical nature. "Steric selectivity" means spatial selection of species based only on the size of the species. "Preselected" means controlled and predetermined.

There are many advantages to the coatings and methods of the present invention. These advantages include: (1) a significant concentration of interaction sites due to the large surface areas (see G. J. Brinker and G. W. Scherer, *Sol-Gel Science*, Academic Press, San Diego, (1990)) for adsorption or chemical bonding of the chemical species to be detected; (2) a controlled pore size (see ibid.) which can be used to prepare films where molecules which are not to be detected can be excluded from the active sites in the film based on steric constraints (i.e., molecules too large to fit into the pores are not sensed); (3) a variability in the chemical nature of the film can be used to prepare films which will bind certain types of chemical species more strongly and to a larger extent than other species which are not to be sensed or detected; (4) an increased durability provided by their ceramic nature (i.e., they can withstand extremes of temperature and pressure as well as withstanding contact with a large number of chemically reactive systems); and (5) a relative constancy of film properties, such as elastic modulus and thickness, with changes in temperature, pressure or chemical environment (as compared with commonly used polymer films).

The invention includes a chemical sensor comprising:
(a) a substrate; and
(b) a coating applied to the substrate which selectively sorbs chemical entities of a size less than a preselected magnitude.

There is also provided a method for selectively detecting the presence of a chemical entity within an environment comprising placing a selective chemical sensor as described above in the environment and detecting the film property changes upon sorption of material onto a substrate/coating composite. When the chemical entity or species is sorbed, the overall mass of the piezoelectric substrate/coating composite increases.

The substrate is chosen based on the sensing mechanism being used. For optical sensors, optical fibers and optical wave guides are useful in accordance with the invention and are known in the art. For piezoelectric sensors, piezoelectric substrate, useful in accordance with the invention are those known in the art, for example, ST-cut quartz. In addition to quartz crystals, piezoelectric ceramics such as those of the barium titanate and lead titanate zirconate families are suitable substrates. These include $LiNbO_3$, $BaTiO_3$ 95 wt % $BaTiO_3$/5% $GaTiO_3$, 80 wt % $BaTiO_3$/12% $PbTiO_3$/8% $CaTiO_3$, $PbNb_2O_6$, $Na_{0.5}K_{0.5}NbO_3$, $Pb_{0.94}Sr_{0.06}(Ti_{0.48}Sr_{0.52})O_3$, and $Pb(Ti_{0.48}Sr_{0.52})O_3$. In some cases, the substrate may comprise a piezoelectric coating material such as ZnO or AlN applied to a non-piezoelectric material such as silicon.

The piezoelectric properties of these and other suitable materials are provided in *CRC Handbook of Materials Science*, Vol. III, Charles T. Lynch, CRC Press: Boca Raton, Fla., p. 198 (1975). For more information regarding piezoelectric materials, see B. Jaffe, et al., *Piezoelectric Ceramics*, Academic Press, New York (1971).

Fluoropolymers such as poly(vinylidene)diflouride and related copolymers are another family of appropriate piezoelectric substrates. See C. G. Ku, et al., *Electrical Properties of Polymers*, Hanser Publishers; Munich, p. 7 (1987).

The substrate is preferably contained within a SAW device, an APM device, or a QCM device. SAW or APM sensor systems comprise a source of alternating voltage which is applied to an interdigital transducer. The interdigital transducer is located on the piezoelectric substrate and, through the application of the alternating voltage, induces the formation of a surface acoustic wave on the substrate or an acoustic plate mode in the substrate. Changes in the propagation velocity or resonance frequency detected by converting the wave into an electrical signal by a second interdigital transducer, provide for the detection of mass changes resulting from substances adsorbing into a film on the piezoelectric crystal.

If the SAW or APM device is operated as the frequency control element in an oscillator circuit, relative changes in frequency $\Delta f/f_o$ reflect perturbations in acoustic wave velocity $\Delta v/v_o$. When mass loading is the dominant perturbation to the SAW, frequency changes can be related to mass loading by $$\Delta f/f_o = k\Delta v/v_o = -kc_m mn,$$

wherein k is the fraction of the path length between the transducers covered by an adsorbing film; $c_m$ is the mass sensitivity of the device (e.g., 125 cm$^2$–/g for a 100 MHz SAW device on an ST-cut quartz crystal); and n and m are, respectively, the number density and mass of the adsorbed molecules.

For example, the frequency stability of a quartz SAW device (about 1 Hz/min. under ideal conditions) operated at 97 MHz results in detection limits on the order of 100 pg/cm$^2$. For a further discussion on SAW devices, see "Characterization of the Surface Area and Porosity of Sol-Gel Films using SAW Devices," G. C. Frye, et al., *Mat. Res. Soc. Symp. Proc.*, Materials Research Co., Pittsburgh, Vol. 121, pp. 349–354 (1988), and *Determination of BET Surface Areas of Porous Thin Films Using Surface Acoustic Wave Devices*, A. J. Ricco, et al., Langmuir, Vol. 5, pp. 273–276 (1989). For a further discussion on APM devices, see S. J. Martin, et al., *Sensors and Actuators*, "Characterization of SH Acoustic Plate Mode Liquid Sensors," Vol. 20, pp. 253–268 (1989).

QCM sensor systems comprise a source of alternating voltage which is applied to two electrodes on opposites sides of a piezoelectric substrate, typically AT-cut quartz. If an oscillator circuit is used, changes in the resonant frequency can be correlated to changes in film properties, specifically the mass of the coating. A detailed discussion of QGM sensors is given in J. Janata, *Principles of Chemical Sensors*, Plenum Press, New York, pp. 56–69 (1989).

The thin film which provides selectivity exhibits molecular sieving properties. In this sense, the thin film, for example, permits the passage into its pores of chemical entities having a certain maximum effective diameter while excluding the passage of all chemical entities having an effective diameter larger than that maximum effective diameter. The species to be detected pass into the pores within the thin film and are sorbed. Their presence in the pores induces a mass change which can be detected at the same time.

The film, with its molecular sieving properties, is preferably inorganic, especially one derived from a sol-gel process.

The chemical sensor of the invention is suitable for selective detection of a variety of compounds, polar and non-polar. For example, the sensor can be employed to detect aliphatic hydrocarbons (e.g., methane, butanes, pentanco, hexanes, iso- and n-octane, etc.), aromatics (e.g., benzene, toluene, zylenes, etc.), chlorinated hydrocarbons (e.g., methylene chloride, chloroform, carbon tetrachloride), alcohols (e.g., methanol, ethanol, 1-butanol, etc.), aliphatic amines, aromatic amines, carbon monoxide, and water. The sensor can also be employed to detect dissolved species, including cations (e.g., $Cu^{2+}$, $Cr^{6+}$, $Ni^{2+}$) and anions (e.g., $CN^-$, $F^-$).

The invention also encompasses embodiments comprising two or more selective chemical sensors. For example, two sensors used in conjunction could establish a range, with both preselected lower and upper limits, for the effective diameter of the chemical entities to be detected.

Furthermore, a plurality of the sensors could be used in a sensor array, with, e.g., associated control devices and software, in a manner similar to the conventional procedures employed with sensor arrays. See, e.g., W. P. Carey, et al., "Multicomponent Analysis Using an Array of Piezoelectric Crystal Sensors," *Analytical Chemistry*, Vol. 59, pp. 1529–1534 (1987). See also, *Analytical Chemistry*, Vol. 60, pp. 541–544 (1988).

After the sensing has taken place, the sensor coating can be purged or cleaned by a second stream, allowing sensing of a new third stream to take place. For example, water- or acid-base solutions could be used as purging or cleaning solutions, depending on the species being detected and the coating. This would be useful for coating materials which exhibit non-reversible binding of the species to be detected under the conditions (e.g., pH) present in the environment to be monitored.

The following example of a coating 10 of the invention (shown in FIG. 1) on a substrate 11 illustrates the advantage of using both size and chemical selectivity for a group of molecular species. Assume that each molecular species has a reactive group (A or B), such as an alcohol or ketone group, which can chemically interact with a chemical group on the coating. In addition, assume that each molecular species has a nonreactive group (C or D), such as a hydrocarbon chain, which dictates the overall size of the molecule. Finally, assume that molecule B-C 12 is to be sensed in the presence of A-G 14, A-D 16, and B-D 18. If the coating 10 has a surface group which provides strong chemical interactions with chemical group B but weak interactions with chemical group A, selective sorption of B containing compounds is obtained (B-C 12 and B-D 18). If the size of the pores 20 is such that group C is small enough to enter the pores 20 but group D is too large, then only C containing species (A-C 14 and B-C 12) can enter the pores 20 and be sorbed. (The arrows show which species could enter the pores 20 or not enter (arrows show deflection) the pores 20.) However, since there is no chemical reactivity with A-C 14, it enters the pores 20 but is not sorbed within the pores 20. Thus, combining chemical with steric selectivity results in only molecule B-G 12 entering the pores and being sorbed. Thus, molecule B-C 12 is effectively discriminated from the other molecules. This example shows that only by using both chemical interaction and size selectivity can a sensor be produced which is sensitive to B-C 12 but insensitive to A-G 14, A-D 16, and B-D 18. Using chemical interactions alone would result in unwanted detection of B-D 18 while size selectivity alone would result in unwanted detection of A-C 14.

As the number of chemical species present is increased, this dual selectivity mechanism becomes even more powerful in making the sensor respond only to one or a small group of chemicals. This same selectivity advantage can be obtained for a wide variety of chemical species; for example, for detecting ionic species in solution (e.g., for electroplating monitors), where chemical interactions such as ligand binding can be used to provide selectivity for a class of ions (i.e., selectivity for a single ion is not typically possible). Since the ionic sizes vary over a significant range, especially when ion hydration is considered, it is possible to choose a pore size such that only a fraction of the ions in this class are able to enter the pores and be detected (e.g., ten ionic species will bind to the ligand but only three are small enough to enter the pores, reducing the number of ions which exhibit unwanted detection from nine to two).

Figure 2:
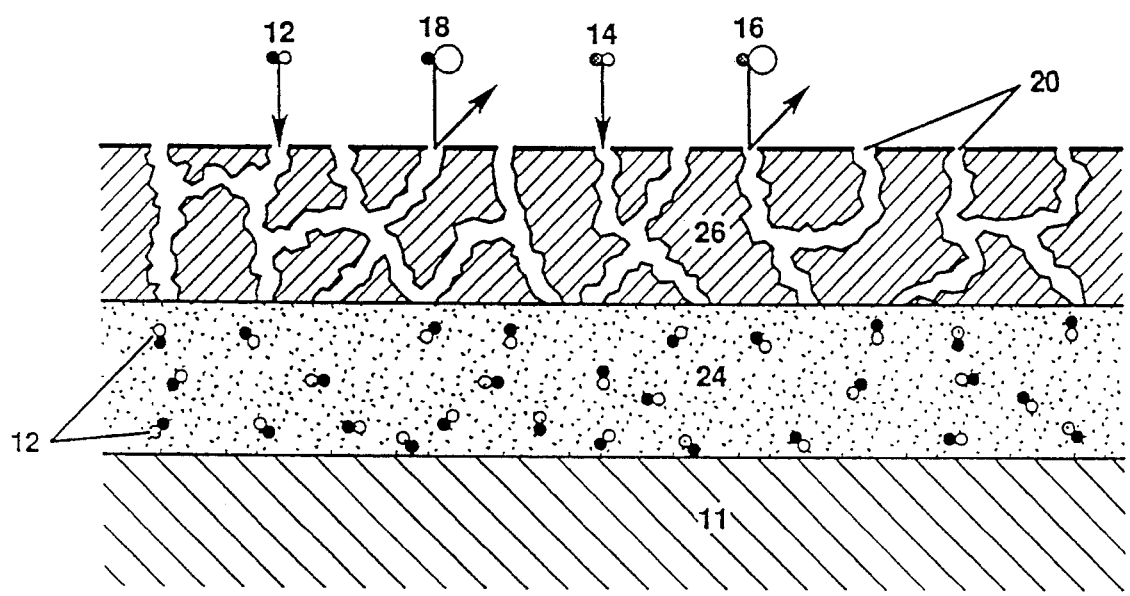
FIG. 2 is an illustration of a multilayer coating of the present invention, providing both steric and chemical selectivity.

In an alternative embodiment, in which it is difficult to form a single-layer coating with the desired chemical properties which has the controlled porosity required to obtain size selectivity, multilayer coatings are useful. For example, as shown in FIG. 2, the sensor substrate 11 is first coated with a film 24 which exhibits chemical interactions providing selective sorption/binding of the chemical species B-G 12 to be detected. This film may be a ceramic film such as described above; however, since controlled porosity is not critical, other types of coatings such as organic polymer films can be used. The sensor is then coated with a controlled porosity film 26 which does not show significant chemical interactions (i.e., low sorption). Since only species A-C 14 and B-C 12 are small enough to penetrate through the controlled porosity film 26 have access to the underlying chemically reactive film 24, both size and chemical interaction can be used to provide selectivity even though a single film capable of both types of selection cannot be formed. As can be seen from FIG. 2, although both species A-C 14 and B-C 12 are small enough to enter the pores 20 in layer 26 (species A-D 16 and B-D 18 are too large), only species B-C 12 will chemically react with layer 24. Thus, species B-C 12 is effectively selected or discriminated from species A-C 14, A-D 16, and B-D 18.

Figure 3A:
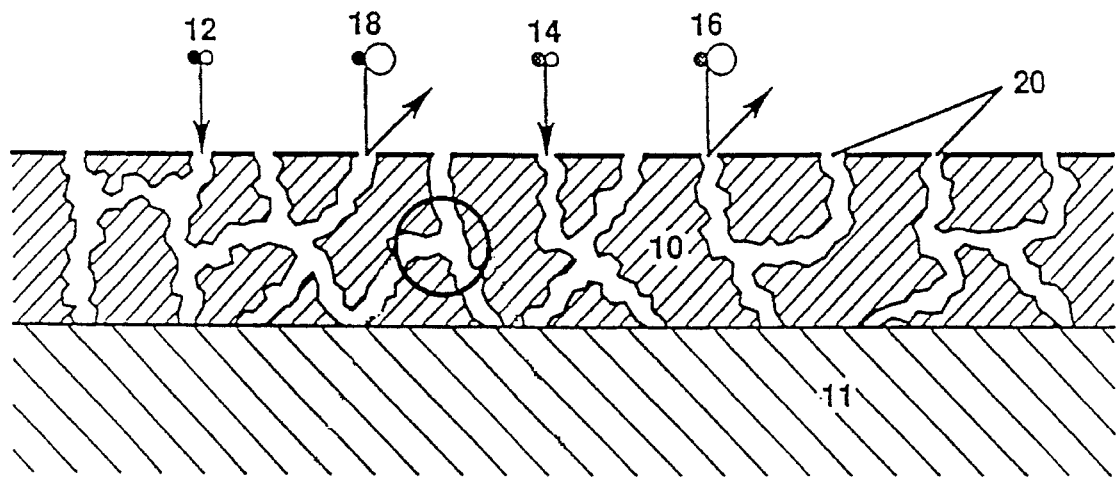
FIGS. 3A and 3B show, respectively, a normal an an exploded view of the use of silane coupling agents in the coating of the present invention.
Figure 3B:
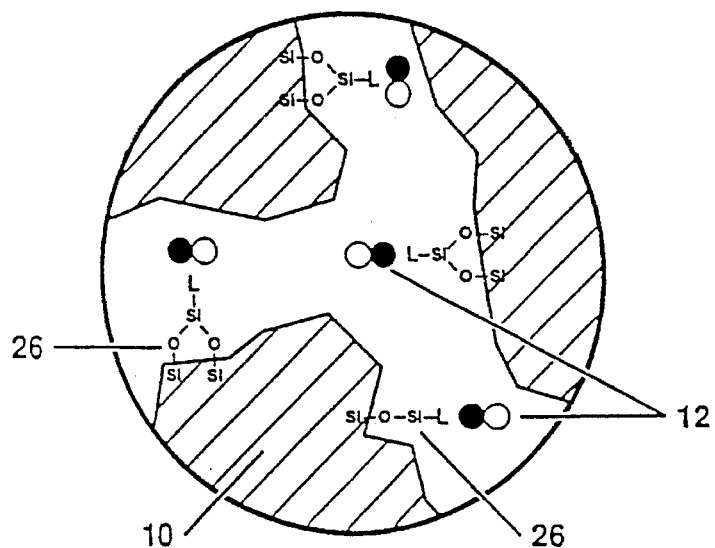

The ability to use sol-gel chemistry to form controlled porosity oxide films has been well demonstrated; however, as deposited, these films exhibit only a minimal amount of selectivity based on chemical interactions. Therefore, one method of the invention for forming these coatings is to alter the chemistry of oxide films to provide this chemical selectivity. Some methods for performing these alterations are as follows:

A. As shown in the exploded view of FIG. 3B, silane coupling agents 26 (i.e., $LSiX_3$ or $LSi(OR)_3$ where X is a halide, OR is an alkoxide group and L is an attached group) can be used to attach chemically reactive groups such as chelating agents (e.g., ethylene diamine, acetylacetonate, and carbamates) to the surfaces of silicate or other oxide materials. Similarly, other coupling agents can be chosen, depending on the substrate material (e.g., species containing phosphonic acids form durable linkages to titanates and zirconates). The large surface area of the silicate or other substrate material 10 results in a large number of attached groups 26. Since these groups stick out away from the surface, the thickness of this attached layer needs to be taken into account when deciding on the optimal pore size 20 for the starting silicate or other substrate material (i.e., the pores 20 need to be larger than the desired size by an amount equal to the thickness of the attached layer).

B. Species such as metal alkyls, can be used in gas phase reactions to replace some of the surface molecules (e.g., Si molecules) with other metals or compounds having different properties (e.g., different acid/base characteristics). For example, trimethylaluminum can be used to provide aluminum (Al) at the surfaces which chemically binds to ammonia and other nitrogen containing compounds.

Figure 4A:
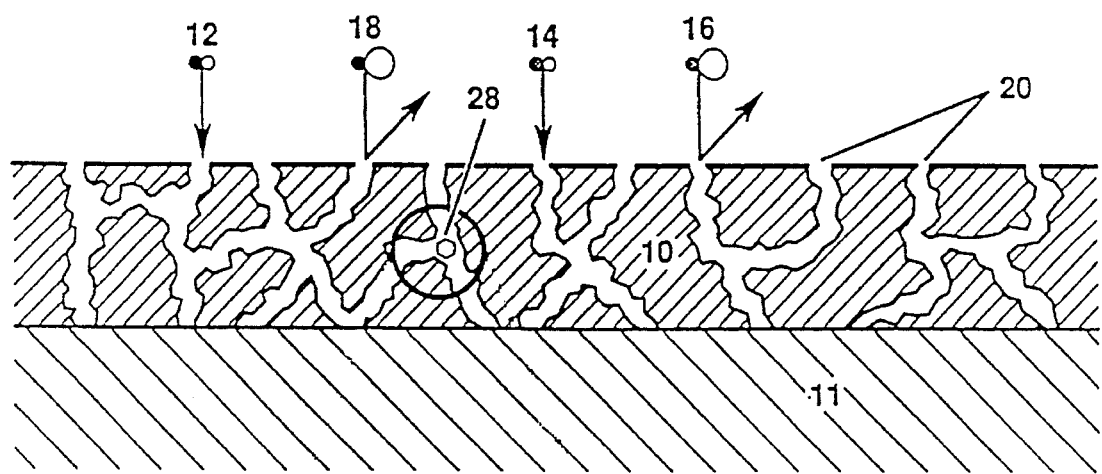
FIGS. 4A and 4B show, respectively, a normal an an exploded view of the use of species within the pores of the coating of the present invention.
Figure 4B:
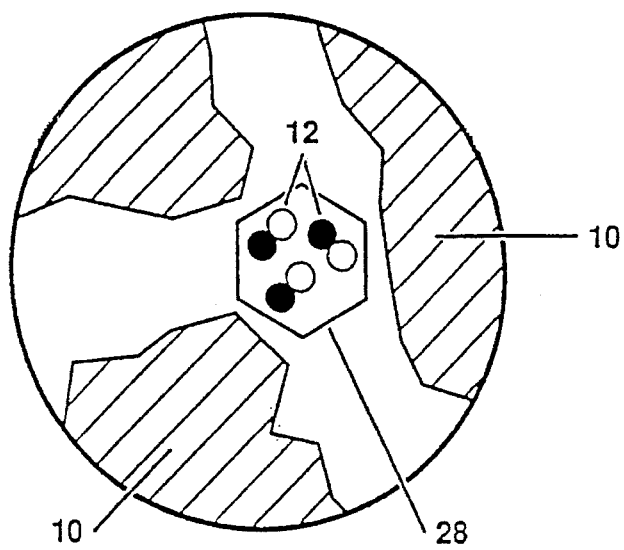

C. As shown in FIG. 4B, species 28 such as polyoxometalate species (metal oxide clusters which exhibit selective ion exchange properties) can be added to the sol-gel solution and deposited along with the oxide film 10. When the size of the pores 20 in the film 10 are controlled properly, these large molecules 28 are "trapped" or seated inside the pores 20 of the oxide matrix of the film and provide the desired chemical interactions. These large molecules 28 may be larger than the entrance to the pores.

In addition to silica, almost all other sol-gel-derived metal oxides and other materials that form thin films are suitable as film materials, including alumina (e.g., from Al-sec-butoxide), boro-aluminosilicate (e.g., from Al-sec-butoxide, Si-tetraethoxide, and trimethyl borate), titania (e.g., from Ti-tetraisopropoxide), and zirconia (e.g., from Zr-tetraisoproxide). Many examples of sol-gel derived metal oxides and non-oxides are given in C. J. Brinker and G. W. Scherer, *Sol-Gel Science*, Academic Press, San Diego (1990) and in "Better Ceramics Through Chemistry III," *Mat. Res. Soc. Symp. Proc.*, Materials Research Society, Pittsburgh, Vol. 121 (1988).

Since sol-gel chemistry can be used with a wide variety of starting materials, the chemical nature of the film can be varied based on the chemical precursors used while the pore sizes can be controlled by varying the reaction and coating conditions. One example of this alternative type of coating is the formation of hydrous oxides such as sodium titanate or sodium niobate. These can be used for ionic species detectors where the acid/base properties of the metal cation (e.g., titanium or niobium) determines the chemical interactions determining selective sorption (due to ion exchange) while the pore size determines which ions have access to the active ion exchange sites. This type of film has the advantage of a single coating step; however, simultaneous optimization of the chemical and microstructural properties is more difficult than for the two step processes outlined above.

Dip- and spin-coating procedures are useful to form the coatings of the invention.

EXAMPLES (INDUSTRIAL APPLICABILITY)

The invention is further illustrated by the following non-limiting examples.

Example 1

Silicate sol-gel films were modified using silane coupling agents. The derivatization of the coating surfaces with ligands that selectively bind chemical species of interest was investigated. See G. C. Frye, et al., "Sol-Gel Coatings on Acoustic Wave Devices: Thin Film Characterization and Chemical Sensor Development," *Mat. Res. Soc. Symp.*, Materials Research Society, Pittsburgh, Vol. 180, pp. 583–593, (1990). The derivatizing agents used were silane coupling agents. The specific agent used, designated TMS-DETA, had a diethylenetriamine (DETA) ligand separated from the Si by a propyl chain:

$$(CH_3O)_3Si(CH_2)_3NH(CH_2)_2NH(CH_2)_2NH_2.$$

The derivation technique involved the preparation of a porous coating from a standard sol-gel solution followed by treatment of the surfaces of the sample with the TMS-DETA (from a dilute solution in ethanol). This technique allowed the desired pore structure (allowing for the decrease in the pore dimensions due to the attached surface layer) to first be formed using already characterized sol-gel protocols. For this technique, particulate silicate films were deposited by spin-coating a solution containing 29 nm diameter particles. X-ray fluorescence analysis indicated that the uptake of $Cu^{2+}$ in the as-deposited film was less than 0.1 µg/cm² of film after a 5 minute treatment in 1M $Cu(NO_3)_2$ followed by rinsing with deionized water. However, after the diethylenetriamine ligands were silane-coupled to the surfaces, the $Cu^{2+}$ uptake from a similar treatment increased to 3.0 µg/cm². Based on the film thickness (800 nm) and the particle diameter, this amount of $Cu^{2+}$ was used to calculate the surface area per DETA molecule (assuming the $Cu^{2+}$ was bound stoichiometrically and that the film was 60% dense).

The value calculated was 0.35 nm² per molecule, which represents about one DETA for every three Si at the surface. Since the silane coupling agent was trifunctional and has the potential to form three siloxane linkages, this value was in good agreement with a full coating of the DETA ligands on the surfaces of the film. Since a wide variety of ligands with silane coupling groups are commercially available, this generic technique is able to provide high surface area coatings with tailored chemical selectivities.

Example 2

Figure 5:
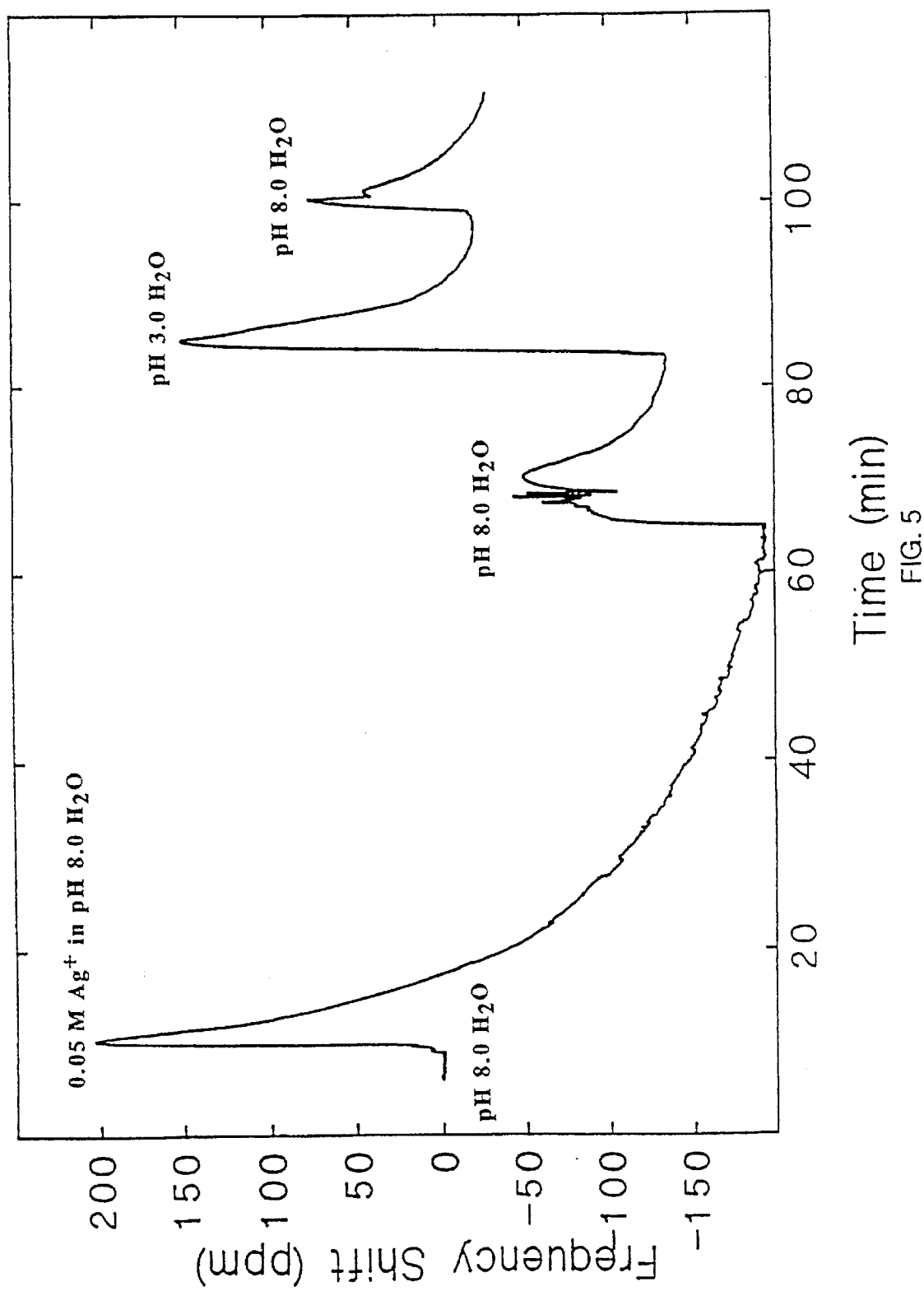
FIG. 5 shows a frequency response of a sodium titanate-coated APM device during the exchange of $Ag^+$.

The utility of the hydrous oxide ion exchange coatings was demonstrated using a coated AW device. (See ibid., and G. C. Frye, et al., "Controlled Microstructure Oxide Coatings for Chemical Sensors," *Proc.* 1990 *Solid-State Sensor and Actuator Workshop*, (IEEE, New York, 1990) p. 61.) The acoustic wave used was an acoustic plate mode (APM) which can be effectively operated in contact with liquids. The sensor response during the uptake and subsequent removal of $Ag^+$ ions from the hydrous titanate coating is shown in FIG. 5. When a pH 8.0 solution of NaOH was replaced with a 0.05M $AgNO_3$ solution at the same pH, a frequency decrease of about 190 ppm was observed after an initial frequency increase. Assuming the frequency response is due to changes in the mass loading of the film, this shift corresponds to a change in the film mass density of 4.4 $\mu g/cm^2$. This value was significantly lower than the value of 70 $\mu g/cm^2$ calculated for complete exchange of $Ag^+$ for $Na^+$ based on the film thickness of 600 nm (two coats were used), a sodium titanate skeletal density of 2.4 $g/cm^3$, 40% porosity and a mass per ion exchange site of 177 g/mole (assumes site has form $HTi_2O_5^-$). This difference may indicate that many of the ion exchange sites are inaccessible. The initial upward spike appears to be due to the loss of liquid flow which occurred during the change of solutions and was observed every time the solutions were changed.

When the pH 8.0 $AgNO_3$ solution was replaced with a NaOH solution at the same pH, a 60 ppm frequency increase was observed indicating that about 30% of the $Ag^+$ was removed from the film. When a pH 3.0 $HNO_3$ solution is used, an additional frequency increase of over 110 ppm was observed. The total frequency increase in these two steps indicates that 90% of the exchanged $Ag^+$ had been removed, verifying the reversibility of this exchange process. Except for the upward spike, a relatively small frequency shift was observed when the pH 3.0 $HNO_3$ solution was replaced with the pH 8.0 NaOH, indicating that the frequency increase seen with the pH 3.0 solution was due to mass loss during $Ag^+$ removal rather than due to some other effect related to the pH change. These results demonstrate that the large ion exchange capacities of hydrous oxide materials can be used to provide large sensor responses. In addition, studies using $Ni^{2+}$ showed much smaller ion exchange values, demonstrating chemical selectivity.

Example 3

Selective cation exchange composites were prepared as follows:

Silicate based sol-gel derived glasses were modified by inclusion of polyoxometalates. Oxometalates function as selective ion-exchangers while sol-gel solutions were used as inclusion materials resulting in processable, stable ion-exchange composites. See K. Moller, et al., *Mat. Res. Soc. Symp. Proc.*, San Francisco (1990).

Ion-exchange powders were used in the form of (a) heteropolyoxometalares, e.g., a variety of Keggin salts $(X_3PM_{12}O_{40})$, wherein X=H, $NH_4$, Rb, or Ag; and M=Mo or W); and (b) Oxometalates, e.g., pyrochlores $NaW_2O_{6.5}$.

Sol-gel based solutions were used in the form of (a) acid or base catalyzed Si-tetraethoxide/ethanol mixtures, and (b) multicomponent solutions (Si-tetraethoxide, Al-sec-butoxide, trimethylborate).

Keggin Composites:

The preparation of these composites was performed in three different ways:

a) by direct synthesis in preformed porous oxides (by suspending a porous oxide in a solution of sodium molybdate or tungstate and phosphoric acid at pH=1.5 and subsequent precipitation of the keggin salts in pores of the oxide with an appropriate counter ion);

b) by preparation of Keggin ions from its components (see a)) in a sol solution; and c) by combination of preprepared Keggin salt powders and a sol solution.

Spectroscopic analysis with FTIR, Raman, and EXAFS (Extended X-ray Absorption Fine Structure Spectroscopy) techniques showed that all three methods result in the inclusion of Keggin ions in the oxide matrix.

Keggin ions are known for their high selectivity for the larger alkaline earth cations (Rb, Cs). The ion-exchange studies performed with pure Keggin powders (e.g., the ammonium salt $(NH_4)_3PM_{12}O_{40})$ in acid solutions (pH=1.5) with Ag, Rb, or Pb-nitrates showed a high exchange ratio when a 10 time excess was offered (>90%; Pb>Ag>Rb). Under stoichiometric conditions 20–50% of Ag or Rb was exchanged. Lead was consumed in excess due to formation of lead molybdate (potential application as a lead dosimeter). Reversibility for the ammonium ion was achieved best with the silver salts (Ag>Rb>Pb).

Exchange studies on Keggin-oxide composites always showed a higher ion exchange capacity compared to the pure Keggin powders (e.g., under stoichiometric conditions, 75% or 95% for Ag or Rb, respectively). This may indicate a higher dispersion of Keggin units in the oxide matrix and therefore an easier access to cation positions. The oxide matrix itself did not show any ion-exchange capacity.

It could be shown by EXAFS spectroscopy that cation positions after ion exchange of pure Keggin powder and of oxide composites are structurally identical.

Pyrochlore Composites:

Pyrochlores were prepared by hydrothermal synthesis from sodium tungstate in aqueous solutions at pH=3.5 and 120° C. The resulting crystalline 3 µm particles were suspended in sol-gel solutions which were subsequently dip-coated onto QMCs. Ion exchange studies on pure pyrochlore powders showed a strong affinity for Tl and Ag (e.g., under stoichiometric conditions 94% exchange of Tl, 82% of Ag). Larger cations, such as Pb, or smaller, divalent cations, such as Cu or Go were nearly completely excluded (e.g., 2% exchange of Cu, 0.1% of Pb). The presence of pyrochlores and their exchange capability in oxide composites could be shown with FTIR, UV-VIS and EXAFS spectroscopy.

The preceding examples can be repeated with similar success by substituting the generically or specifically described reactants and/or operating conditions of this invention for those used in the preceding examples.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

What is claimed is:

1. A coating for providing both size selectivity and chemical selectivity among different chemical species, the chemical species comprising analyte species of larger size and analyte species of smaller size, the analyte species of smaller size comprising analyte species having either a predetermined chemical reactivity or a predetermined chemical non-reactivity, said coating comprising:

one or more layers comprising size selectivity means followed by chemical selectivity means wherein said chemical selectivity of the analyte species occurs only after said size selectivity of the analyte species;

wherein the layer which comprises said size selectivity means comprises pores having a predetermined uniform pore size, said predetermined uniform pore size sufficient to prevent the analyte species of larger size than said pores from entering said pores and said predetermined uniform pore size sufficient to allow the analyte species of smaller size than said pores to enter said pores;

wherein the layer which comprises said chemical selectivity means comprises chemical reaction sites for chemically sorbing the analyte species of smaller size with the predetermined chemical reactivity entering said pores and not chemically sorbing the other analyte species of smaller size with the predetermined chemical non-reactivity entering said pores;

wherein said coating provides selectivity of the analyte species of smaller size having the predetermined chemical reactivity from the analyte species of larger size and from the analyte species of smaller size having the predetermined chemical non-reactivity; and wherein said coating comprises a sol-gel coating comprising said predetermined uniform pore size.

2. The invention of claim 1 wherein said coating comprises a single layer for providing both said size selectivity means and said chemical selectivity means.

3. The invention of claim 2 wherein said single layer comprises said chemical reaction sites within said pores for chemically sorbing the analyte species of smaller size with the predetermined chemical reactivity entering said pores.

4. The invention of claim 3 wherein said chemical reaction sites for chemically sorbing the analyte species of smaller size with the predetermined chemical reactivity entering said pores are disposed adjacent the coating layer and seated within said pores.

5. The invention of claim 4 wherein said chemically reactive species are trapped within said pores due to their size being larger than the size of the entrance to said pores.

6. The invention of claim 4 wherein said chemically reactive species seated within said pores exhibit selective ion exchange properties.

7. The invention of claim 4 wherein said chemically reactive species seated within said pores comprise polyoxometalate species.

8. The invention of claim 1 wherein said chemical reaction sites in said chemical selectivity layer comprises a chemically reactive species attached to said layer, said chemically reactive species reactive to the analyte species with the predetermined chemical reactivity of smaller size entering said pores.

9. The invention of claim 8 wherein said chemically reactive species comprises a chelating agent.

10. The invention of claim 1 wherein said coating comprises a hydrous oxide.

11. The invention of claim 10 wherein said hydrous oxide coating comprises at least one member selected from the group consisting of sodium titanate and sodium niobate.

12. The invention of claim 1 wherein said coating comprises multiple layers.

13. The invention of claim 12 wherein at least one layer provides said pores for said size selectivity means and at least one other layer provides said chemical reaction sites for said chemical selectivity means.

14. The invention of claim 1 wherein said coating comprises at least one member selected from the group consisting of silicate films, titanate films, zirconate films, and alumina films.

15. The invention of claim 1 wherein a portion of surface molecules in said chemical selectivity layer is replaced with chemically reactive species, said chemically reactive species reactive to the analyte species of smaller size with the predetermined chemical reactivity entering said pores.

16. The invention of claim 1 wherein said coating has a thickness of between approximately 0.1 μm and 10 μm.

17. A coating for providing both size selectivity and chemical selectivity among different chemical species, the chemical species comprising analyte species of larger size and analyte species of smaller size, the analyte species of smaller size comprising analyte species having either a predetermined chemical reactivity or a predetermined chemical non-reactivity, said coating comprising:

one or more layers comprising size selectivity means followed by chemical selectivity means wherein said chemical selectivity of the analyte species occurs only after said size selectivity of the analyte species;

wherein the layer which comprises said size selectivity means comprises pores having a predetermined uniform pore size, said predetermined uniform pore size sufficient to prevent the analyte species of larger size than said pores from entering said pores and said predetermined uniform pore size sufficient to allow the analyte species of smaller size than said pores to enter said pores;

wherein the layer which comprises said chemical selectivity means comprises chemical reaction sites for chemically sorbing the analyte species of smaller size with the predetermined chemical reactivity entering said pores and not chemically sorbing the other analyte species of smaller size with the predetermined chemical non-reactivity entering said pores;

wherein said coating provides selectivity of the analyte species of smaller size having the predetermined chemical reactivity from the analyte species of larger size and from the analyte species of smaller size having the predetermined chemical non-reactivity; and wherein said chemical reaction sites comprise a metal as chemically reactive species.

18. The invention of claim 17 wherein said metal comprises aluminum.

19. A selective chemical sensor comprising a coating disposed on a sensor substrate, said coating providing for both size selectivity and chemical selectivity among different chemical species, the chemical species comprising analyte species of larger size and analyte species of smaller size, the analyte species of smaller size comprising analyte species having either a predetermined chemical reactivity or a predetermined chemical non-reactivity, said coating comprising:

one or more layers comprising size selectivity means followed by chemical selectivity means wherein said chemical selectivity of the analyte species occurs only after said size selectivity of the analyte species;

wherein the layer which comprises said size selectivity means comprises pores having a predetermined uniform pore size, said predetermined uniform pore size sufficient to prevent the analyte species of larger size than said pores from entering said pores and said predetermined uniform pore size sufficient to allow the analyte species of smaller size than said pores to enter said pores;

wherein the layer which comprises said chemical selectivity means comprises chemical reaction sites for chemically sorbing the analyte species of smaller size with the predetermined chemical reactivity entering said pores and not chemically sorbing the other analyte species of smaller size with the predetermined chemical non-reactivity entering said pores;

wherein said coating provides selectivity of the analyte species of smaller size having the predetermined chemical reactivity from the analyte species of larger size and from the analyte species of smaller size having the predetermined chemical non-reactivity and wherein said substrate comprises a piezoelectric substrate capable of detecting mass changes resulting from sorption of material thereon.

20. The invention of claim 19 wherein said substrate comprises a piezoelectric substrate capable of detecting mass changes resulting from sorption of material thereon.

21. The invention of claim 20 further comprising means for generating an alternating voltage which is applied to an interdigital transducer connected to said piezoelectric surface.

22. The invention of claim 20 wherein said piezoelectric element comprises a member selected from the group consisting of a surface acoustic wave (SAW) device, an acoustic plate mode (APM) device, and a quartz crystal microbalance (QCM) device.

23. The invention of claim 20 wherein said piezoelectric surface comprises a member selected from the group consisting of quartz crystal, $LiNbO_3$, $BaTiO_3$, 95 wt % $BaTiO_3$/5% $CaTiO_3$, 80 wt % $BaTiO_3$/12% $PbTiO_3$/8% $CaTiO_3$, $PbNb_2O_6$, $Na_{0.5}K_{0.5}NbO_3$, $Pb_{0.94}Sr_{0.06}(Ti_{0.48}Sr_{0.52})O_3$, $Pb(Ti_{0.48}Sr_{0.52})O_3$, ZnO, AlN, and polyvinylidene diflouride.

* * * * *